US011055851B2

(12) United States Patent
Novikov et al.

(10) Patent No.: US 11,055,851 B2
(45) Date of Patent: Jul. 6, 2021

(54) MULTI-CLASS IMAGE SEGMENTATION METHOD (71) Applicants: Agfa Healthcare NV, Mortsel (BE); VRVIS ZENTRUM FÜR VIRTUAL REALITY UND VISUALISIERUNG, Vienna (AT)

(72) Inventors: Alexey Novikov, Mortsel (BE); David Major, Mortsel (BE); Dimitrios Lenis, Mortsel (BE); Maria Wimmer, Mortsel (BE); Katja Buehler, Mortsel (BE)

(73) Assignees: Agfa HealthCare NV, Mortel (BE); VRVis Zentrum für Virtual Reality und Visualisierung, Vienna (AT)

( * ) Notice: Subject to any disclaimer, the term of this patent is extended or adjusted under 35 U.S.C. 154(b) by 84 days.

(21) Appl. No.: 16/479,626

(22) PCT Filed: Jan. 24, 2018

(86) PCT No.: PCT/EP2018/051632
§ 371 (c)(1),
(2) Date: Jul. 22, 2019

(87) PCT Pub. No.: WO2018/138104
PCT Pub. Date: Aug. 2, 2018

(65) Prior Publication Data
US 2021/0019889 A1 Jan. 21, 2021

(30) Foreign Application Priority Data
Jan. 27, 2017 (EP) .................................. 17153431

(51) Int. Cl.
*G06T 7/11* (2017.01)
*G06K 9/62* (2006.01)
(Continued)

(52) U.S. Cl.
CPC .............. *G06T 7/11* (2017.01); *G06K 9/6232* (2013.01); *G06N 3/04* (2013.01); *G06N 3/08* (2013.01);
(Continued)

(58) Field of Classification Search
None
See application file for complete search history.

(56) References Cited

U.S. PATENT DOCUMENTS 10,304,002 B2\* 5/2019 Brunner ................ G06F 3/0304
2011/0007954 A1\* 1/2011 Suehling ............ G06K 9/00362
382/128

(Continued)

FOREIGN PATENT DOCUMENTS

EP 3 273 387 \* 7/2016
EP 3 355 270 \* 1/2017

OTHER PUBLICATIONS

Brosch, Tom, et al. "Deep convolutional encoder networks for multiple sclerosis lesion segmentation." International Conference on Medical Image Computing and Computer-Assisted Intervention. Springer, Cham, 2015. (Year: 2015).\*

(Continued)

*Primary Examiner* — Andrae S Allison
(74) *Attorney, Agent, or Firm* — Stinson LLP (57) ABSTRACT

A pipe-line method for multi-label segmentation of anatomic structures in a medical image using a convolutional neural network trained with a weighted loss function takes into account under—representation of at least one anatomical structure in a ground-truth mask relative to other anatomical structures. Different architectures for the convolutional neural network are described.

9 Claims, 6 Drawing Sheets (51) Int. Cl.
*G06N 3/04* (2006.01)
*G06N 3/08* (2006.01)
*G06T 7/00* (2017.01)
*A61B 5/055* (2006.01)
*A61B 6/00* (2006.01)
*A61B 8/08* (2006.01)

(52) U.S. Cl.
CPC ............ *G06T 7/0012* (2013.01); *A61B 5/055* (2013.01); *A61B 6/5252* (2013.01); *A61B 8/5215* (2013.01); *G06T 2207/20076* (2013.01); *G06T 2207/20081* (2013.01); *G06T 2207/20084* (2013.01); *G06T 2207/30048* (2013.01); *G06T 2207/30061* (2013.01)

(56) References Cited

U.S. PATENT DOCUMENTS

| | | | | |
|---|---|---|---|---|
| 2018/0300882 | A1* | 10/2018 | Kim | G06T 7/11 |
| 2019/0205606 | A1* | 7/2019 | Zhou | G06N 3/0445 |
| 2020/0320752 | A1* | 10/2020 | Chen | G06N 3/08 |

OTHER PUBLICATIONS

Srivastava et al, Dropout: A Simple Way to Prevent Neural Networks from Overfitting, Journal of Machine Learning Research 15 (2014) 1929-1958 Submitted Nov. 2013; Published Jun. 2014 (Year: 2014).*

J. U. Kim, H. G. Kim and Y. M. Ro, "Iterative deep convolutional encoder-decoder network for medical image segmentation," 2017 39th Annual International Conference of the IEEE Engineering in Medicine and Biology Society (EMBC), Seogwipo, 2017, p. 685-688, doi: 10.1109/EMBC.2017.8036917. (Year: 2017).*

V. Badrinarayanan, A. Kendall and R. Cipolla, "SegNet: A Deep Convolutional Encoder-Decoder Architecture for Image Segmentation," in IEEE Transactions on Pattern Analysis and Machine Intelligence, vol. 39, No. 12, pp. 2481-2495, Dec. 1, 2017, doi: 10.1109/TPAMI.2016.2644615. (Year: 2017).*

Ronnebergeretal, U-Net: Convolutional Networks for Biomedical Image Segmentation, home page: http://lmb.informatik.uni-freiburg.de/ May 18, 2015 (Year: 2015).*

Official Communication issued in International Patent Application No. PCT/EP2018/051632, dated Feb. 22, 2018.

Brosch et al., "Deep Convolutional Encoder Networks for Multiple Sclerosis Lesion Segmentation", Springer International Publishing, Nov. 18, 2015, pp. 3-11.

Tsujii et al., "Automated segmentation of anatomic regions in chest radiographs using an adaptive-sized hybrid neural network", Medical Physics, vol. 25, No. 6, Mar. 25, 1998, 12 pages.

Cernazanu-Glavan et al., "Segmentation of bone structure in X-ray images using convolutional neural network", Advances in Electrical and Computer Engineering, vol. 13. No. 1, Feb. 2013, pp. 1-8.

Carneiro et al., "The Segmentation of the Left Ventricle of the Heart From Ultrasound Data Using Deep Learning Architectures and Derivative-Based Search Methods", IEEE Transactions on Image Processing, vol. 21, No. 3, Mar. 2012, pp. 968-982.

Havaei et al., "Brain tumor segmentation with Deep Neural Networks", Medical Image Analysis, May 11, 2016, pp. 18-31.

Petersen et al,. "Breast Tissue Segmentation and Mammographic Risk Scoring Using Deep Learning", Springer Science & Business Media B.V., Springer International Publishing, 2014, 9 pages.

Gaonkar et al., "Deep learning in the small sample size setting: cascaded feed forward neural networks for medical image segmentation", Proceedings of SPIE, vol. 9785, Mar. 24, 2016, 10 pages.

Long et al., "Fully Convolutional Networks for Semantic Segmentation", Proceedings of the IEEE Conference on computer Vision and Pattern Recognition, 2015, pp. 3431-3440.

Ronneberger et al., "U-net: Convolutional Networks for Biomedical Image Segmentation", International Conference on Medical Image Computing and Comptuer Assisted Intervention, Springer International Publishing, 2015, pp. 234-241.

* cited by examiner

| Architecture | # of parameters | CPU(s) | GPU(s) | Pros | Cons |
|---|---|---|---|---|---|
| InvertedNet | 3 140 771 | 7.1 | 0.06 | Small # of parameters, best performance | Slow testing time |
| All-Convolutional | 34 512 388 | 4.2 | 0.03 | Learns pooling, simple all-convolutional architecture | Large # of parameters |
| All-Dropout | 31 377 988 | 4.1 | 0.03 | Fastest model, simple architecture | Large # of parameters |
| J-Net | 31 895 172 | 3.9 | 0.05 | Fast, improves results for low resolutions | Large # of parameters |

| Bodypart | Lungs | | | Clavicles | | | Heart | | |
|---|---|---|---|---|---|---|---|---|---|
| Evaluation metric | D | J | $S_{sg}$ | D | J | $S_{sg}$ | D | J | $S_{sg}$ |
| Training 90%, Validation 10% | 0.970 | 0.943 | 0.75 | 0.901 | 0.820 | 0.98 | 0.937 | 0.881 | 1.90 |
| Training 70%, Validation 30% | 0.970 | 0.943 | 0.81 | 0.899 | 0.817 | 1.87 | 0.934 | 0.876 | 1.99 |
| Training 50%, Validation 50% | 0.972 | 0.945 | 0.76 | 0.896 | 0.812 | 1.52 | 0.928 | 0.865 | 2.07 |
| Training 30%, Validation 70% | 0.968 | 0.939 | 0.85 | 0.866 | 0.764 | 2.56 | 0.924 | 0.859 | 2.20 |
| Training 10%, Validation 90% | 0.948 | 0.901 | 1.01 | 0.805 | 0.674 | 2.88 | 0.875 | 0.778 | 2.96 |

FIG. 5

| Bodypart | Lungs | | | Clavicles | | | Heart | | |
|---|---|---|---|---|---|---|---|---|---|
| Evaluation metric | D | J | $S_{sg}$ | D | J | $S_{sg}$ | D | J | $S_{sg}$ |
| Training 90%, Validation 10% | 0.969 | 0.941 | 1.15 | 0.928 | 0.866 | 0.58 | 0.940 | 0.887 | 2.33 |
| Training 70%, Validation 30% | 0.971 | 0.944 | 0.96 | 0.931 | 0.871 | 0.55 | 0.932 | 0.872 | 2.56 |
| Training 50%, Validation 50% | 0.972 | 0.946 | 0.73 | 0.920 | 0.853 | 1.10 | 0.932 | 0.873 | 1.98 |
| Training 30%, Validation 70% | 0.961 | 0.925 | 1.41 | 0.906 | 0.828 | 0.65 | 0.914 | 0.842 | 3.31 |
| Training 10%, Validation 90% | 0.940 | 0.887 | 2.06 | 0.837 | 0.719 | 1.30 | 0.875 | 0.778 | 4.30 |

MULTI-CLASS IMAGE SEGMENTATION METHOD

CROSS REFERENCE TO RELATED APPLICATIONS

This application is a 371 National Stage Application of PCT/EP2018/051632, filed Jan. 24, 2018. This application claims the benefit of European Application No. 17153431.6, filed Jan. 27, 2017, which is incorporated by reference herein in its entirety.

BACKGROUND OF THE INVENTION

1. Field of the Invention

The present invention relates to image segmentation. More specifically the invention relates to a method for synchronous multi-class segmentation of different anatomical structures in medical images, such as segmentation of lung, heart and clavicles in chest radiographs.

2. Description of the Related Art

The invention relates to synchronous multi-class segmentation of different anatomical structures.

Multi-class segmentation can for example be used to segment different anatomical structures in a medical image such as lungs, heart and clavicles in a chest radiograph.

Other applications can be envisaged such as segmentation of lesions, e.g. lesions due to tuberculosis, segmentation of ribs etc.

In general, the invention aims at multi-class segmentation of structures having clear borders in medical images.

As the result of such a segmentation process, variations of the size, position and areas of heart, lung fields, hila structure, clavicles etc. may be detected.

This may give clues on existing conditions like TBC and cancer or help in further steps of computer aided detection and medical diagnosis.

Hence, semantic segmentation of radiographs, i.e. the localisation of organs or structures has been an active field of study.

Individual anatomical intricacies like high inter-personal variations in shape and size of central organs like lung fields, clavicles and heart, related to age, size and gender, ambiguous organ boundaries due to organ overlaps and artifacts caused by movements and image modality intrinsics, are just a few of the reasons why accurate organ segmentation remains an inherently challenging task.

Classical algorithmic approaches have been widely described and used. The space of algorithmic approaches may be roughly partitioned into rule-, shape- and graph-based methods, pixel classification and statistical approaches.

Each methodological framework has its own set of advantages, e.g. by limiting to a predefined rule-set or deformable shape, rule and shape based methods will yield anatomical sound solutions.

While conceptually more than 50 years old, neural networks (NN), the abstracted basis of deep learning, are living through a revival. A deeper understanding of training and numerical behavior and the steep increase of tractable calculation schemes through the leveraging of graphical processing units (GPU)s has allowed this class of approach to become the de facto standard, or at least serious contender in several machine learning branches.

The following focuses on convolutional neural networks (CNN), an often successfully used subclass of NN in computer vision tasks.

A prototypical setup of such a CNN consists of a combination of convolution filters, interspersed with data reduction and pooling layers. The driving idea is to mimic human visual cognition, in that sense that the complete picture, is derived out of low-level features, e.g. edges and circles, which in return yield more distinctive features and finally the desired target through recombination in each successive layer. In that regard the main difference to classical approaches is that deep learning typically avoids using specific, manually engineered features for a purely derived set, more capable of describing different aspects of an object.

Regarding the segmentation of medical images several such setups have been studied. Typically, CNNs are used for classification tasks, i.e. an input image is assigned to a countable set of class labels. Complicating, medical images long for the spatial relation of this class labels. As stated above this semantic segmentation typically builds upon a vast set of training data. Such deep datasets are not typical for the medical domain, rendering most current approaches unfeasible, hence calling for a finely tailored strategy.

First attempts date back more than 15 years ago. Tsujii et al. "Automated segmentation of anatomical regions in chest radiographs using an adaptive-sized hybrid neural network, "Medical physics, vol. 25, pp. 998-1007, 1998, use a NN for lung field segmentation yielding in accuracy around 86%. Aece et al. "Segmentation of bone structure in x-ray images using convolutional neural network", Advances in Electrical and Computer Engineering, vol. 13, no. 1, pp. 87-94, February 2013, use a CNN as a binary classifier and thereby partition chest radiographs into the two {bone, non-bone} sets in a fully-automated fashion. NN do not need to be considered as a standalone solution as T. A. Ngo and G. Carneiro, "Lung segmentation in chest radiographs using distance regularized level set and deep-structured learning and inference," in Image Processing (ICIP, 2015 IEEE International Conference on, September 2015, pp. 2140-2143 demonstrates. The group combined regularized level set with a deep learning approach and yielded on JSRT an overlap score of 0.948-0.985.

While CXR segmentation has not been covered extensively yet, different modalities like ultrasound, CT and MRT have been explored [G. Carneiro, J. C. Nascimento, and A. Freitas, "The segmentation of the left ventricle of the heart from ultrasound data using deep learning architectures and derivative-based search methods", IEEE Transactions on Imaging Processing, vol. 21, no. 3, pp. 968-982, March 2012; M. Havaei, A. Davy, D. Warde-Farley, A. Biard, A. Courville, Y. Bengio, C. Pal, P.-M. Jodoin and H. Larochelle, "Brain tumor segmentation with deep neural networks," Medical Image Analysis, 2016; P. Petersen, M. Nielsen, P. Diao, N. Karssemeijer, and M. Lillholm, Breast tissue segmentation and mammographic risk scoring using deep learning. Springer Science+Business Media B.V., 2014, pp. 88-94; B. Gaonkar, D. Hovda, N. Martin and L. Macyszyn, "Deep learning in the small sample size setting; cascaded feed forward neural networks for medical image segmentation," pp. 978521-978521-8, 2016].

In J. Long, E. Shelhamer, and T. Darrell, "Fully convolutional networks for semantic segmentation," in Proceedings of the IEEE Conference on Computer Vision and Pattern Recognition, 2015, pp. 3431-3440 addresses the need for local features that coincide with global structures, and defines the Fully Convolutional Net. This type of network allows for arbitrary sized input and output. Starting with the input-layer, every successive layer outputs a three dimensional matrix which values correspond to path-connected fields of the proceeding layer. These fields are respectively convolved, pooled or generally non-linearly transformed, yielding in a contracting series of layers. In combination with layer fusion, i.e. shortcuts between selected layers, this setup achieves a nonlinear, local-to-global feature representation, and allows for pixelwise classification. By adapting this network-class with successive upsampling layers, i.e. enlarging the field of view of the convolution, Ronneberger et al. "U-net: Convolutional networks for biomedical image segmentation," in International Conference on Medical Image Computing and Computer-Assisted Intervention, Springer, 2015, pp. 234-241, can guide the resolution of feature extraction, and thereby control the local-to-global relations of features.

SUMMARY OF THE INVENTION

It is an aspect of this invention to adapt this approach for chest radiographs, i.e. for organ level datasets.

It is a further aspect to adapt this system so that it can be successfully applied for multi-label segmentation of unbalanced data sets and that it can provide very good segmentation results with a reasonable amount of computational effort.

The above-mentioned aspects are obtained by a method having the specific features set out below.

Specific features for preferred embodiments of the invention are also set out below.

The invention has the following advantages over the prior art:

The method of the present invention is very adequate for multi-label synchronous segmentation of anatomical organs in chest radiographs, in particular, clavicles, lung and heart fields.

In specific embodiments of the present invention a number of specific network architectures are introduced that are capable to perform well without additional data augmentation, only on the given data.

These architectures outperform state-of-the art algorithms and original U-Net on the publicly available JSRT dataset.

These architectures are all multi-class and segment lungs, clavicles and heart simultaneously.

Furthermore, these architectures perform effectively on a dataset with highly imbalanced data representation, such as clavicles which are under-represented in the chest radiographs comparing to heart and lung fields.

To solve the problem of imbalanced data representation, two specific weighted loss functions are introduced for the network training procedure.

Further advantages and embodiments of the present invention will become apparent from the following description and drawings.

BRIEF DESCRIPTION OF THE DRAWINGS

FIG. 1(a)-(d) show different embodiments of network architectures.

DETAILED DESCRIPTION OF THE PREFERRED EMBODIMENTS

Like most deep learning related pipelines, the present approach consists of the following main steps: data preparation and normalization, designing model architecture, model training and testing of the trained model. The input in case of chest radiographs consists of a set of 2D images (below called J) and the corresponding multi-channel ground-truth masks. The model is built, initialized and further trained. After the training is finished the learnt model weights and regularization layers are fixed and the model is validated on a set of test images.

Multi-Class Approach

The input consists of a set of 2D images $J=\{I/I \in R^{m_1 \times m_2}\}$ and the corresponding multi-channel binary ground-truth masks $(L_{i,I})_{1 \leq i \leq n}$, n is the number of classes we aim to where $L_i \in R(\{0,1\})^{m_1 \times m_2}$ address, and $m_1$, $m_2$ are the image dimensions.

We first split J into sets $I_{TRAIN}$ of size $K=|I_{TRAIN}|$ and $I_{TEST}=J\backslash I_{TRAIN}$. As described above, for each $I \in J$ a series of binary ground-truth masks $(L_{i,I})_{1 \leq i \leq n}$ is used. For a later reference let C be the set of all ground truth classes, hence $1 \leq n \leq |C|$.

The networks are trained in the following manner: the network is consecutively passed with minibatches $K \in N$ where N is a partition of $I_{TRAIN}$ and minibatches K are non-empty sets of images derived in a way that every image $I \in I_{TRAIN}$ is included in one and only one of the minibatches K. Additionally, we introduce $c_K$ to define the total pixel count over all $I \in K$.

For each $I \in K$ the multi-class output of the network is calculated, i.e. understanding the network as a function $$F: J \to (R(\{0,1\})^{m_1 \times m_2})_{1 \leq i \leq n} \qquad (1)$$

Therefore, for each pixel of I its semantic class $l \in C$ can be derived in a single step up to some probability.

To estimate and maximize this probability we can define an energy function $$\Lambda_{(L_{i,I})}: R(\{0,1\})^{m_1 \times m_2} \times (L_{i,I}) \to R \qquad (2)$$

that estimates the deviation (error) of the network outcome from the desired ground-truth. The error is back-propagated then to update the network parameters. The whole procedure continues until the defined given stopping criteria are fulfilled.

At testing time an unseen image $I \in I_{TEST}$ is passed through the network and the multi-label output F(I) is produced. As defined above, network output consists of series of multi-channel segmentation masks. The channels in case of chest radiographs correspond to different body organs.

The model is built, initialized and further trained. After the training is finished the learnt model weights and regularization layers are fixed and the model is validated on a set of test images. Main steps of the method are introduced in the following sections in detail.

Base Set-Up

The U-Net like architecture which was originally proposed by Ronneberger et al. "U-net: Convolutional networks for biomedical image segmentation," in International Conference on Medical Image Computing and Computer-Assisted Intervention, Springer, 2015, pp. 234-241 consists of contraction and expansion parts. In the contraction part, high-level abstract features are extracted by consecutive application of pairs of convolutional and pooling layers. In the expansion part the upsampled features are merged with the features from the contractive part respectively. The output of the network is a multi-channel segmentation mask where each channel has the same size as the input image.

Excellent performance of the original U-Net architecture has been demonstrated for cell tracking and segmentation of neuronal structures in electron microscopic stacks.

For other subject-specific tasks it however requires additional modifications due to a different data representation when data is highly imbalanced or in cases when data augmentation is not reasonable.

The problem on imbalanced data in medical images occurs due to different sizes of anatomical organs of interest. For example, in JSRT data set ground-truth masks 60% of pixels belong to background, 29% to lung, 2% to clavicles and 9% to heart respectively, hence emphasizing lung and heart fields over clavicles.

Improvements of U-Net Model for Chest Radiographs

On top of the original architecture the network with multiple modifications in regularization, training and architecture is analyzed and evaluated. In each category, a number of possible improvements of the network model are considered in detail and based on the evaluation results a number of models is proposed tailored to efficiently train and perform multiclass segmentation on medical CXR images. To avoid the data augmentation used in the work by Ronnenberger et al. "U-net: Convolutional networks for biomedical image segmentation," in International Conference on Medical Image Computing and Computer-Assisted Intervention, Springer, 2015, pp. 234-241 it is proposed to slightly alternate the model differently by using a different more aggressive regularization. On top of this several architectures are proposed to further improve the segmentation result. In additional to a different model regularization and architectural modifications a different training loss function strategy is proposed to cope with a problem of highly imbalanced data representation.

Architectural Modifications

Acquiring more training data would be of benefit for any learning algorithm in the most cases. However, in medical imaging getting additional data is not always feasible.

Ronnenberger et al. "U-net: Convolutional networks for biomedical image segmentation," in International Conference on Medical Image Computing and Computer-Assisted Intervention, Springer, 2015, pp. 234-241 used elastic deformations for data augmentation in order to regularize the model. However elastic deformations are not reasonable in case of chest radiographs because they would make rigid organs such as lungs, heart and clavicles look anatomically incorrect and could then confuse training by making the network learning features corresponding to unrealistic structures.

The number of feature maps and layers in the original version of U-Net is large which results in tens of millions of parameters in the system which slows down training and does not necessarily decrease generalization error. Without any regularization training of such large networks can overfit on the data. Especially when there is not much training data available. On the CXR data overfitting is a problem especially for smaller or thinner prolonged anatomical organs such as clavicles due to their more varying shape representations in CXR images. In the case when the network architecture is deep and availability of training data is limited, another possibility to decrease the generalization test error of the algorithm is more aggressive regularization.

a) All-Dropout: Simple Fully Regularized Architecture

Dropout layer [29] is a common practice in modern deep network architectures. Moreover, it has been shown by Bouthillier et al. [30] that it can also play a role of data augmentation at the same time. We therefore propose an architecture with a dropout layer after every convolutional layer in the network. We use the Gaussian dropout which is equivalent to adding a Gaussian distributed random variable with zero mean and standard deviation equal to the activation of the neural unit. According to Srivastava et al. "Dropout: a simple way to prevent neural networks from overfitting" Journal of Machine Learning Research, vol. 15, no. 1, pp. 1929-1958, 2014, it works perhaps even better than the classic one which uses the Bernoulli distribution. Besides, adding such noise is a more natural choice for chest radiographs due to noise occurring during their acquisition [31]. In the following this architecture is called All-Dropout.

b) J-Net: Improving Accuracy for Lower Resolution

Smaller objects are hard to segment especially in case of a low image resolution. In this case four pooling layers of the original U-Net architecture can be fatal for such objects.

To deal with this problem on the lower resolution an architecture is proposed which is in the following called J-Net. In this architecture, the All-Dropout is preceded by four convolutional and two pooling layers. The input layer resolution in this case should then be four times larger in each dimension than at the normal input layer resolution.

c) InvertedNet: Improving Accuracy with Fewer Parameters

One way of dealing with model overfitting is to reduce the number of parameters. A modification of the All-Dropout architecture is proposed by a) performing the delayed subsampling of the first pooling layer with (1, 1) pooling and b) changing the numbers of feature maps in the network.

In this architecture, we propose to start with a large number of feature maps and reduce it by a factor by the factor of two after every pooling layer and then increase back by the factor of two after every up-sampling layer.

In this case the networks learn many different variations of structures at early layers and less high level features at the later layers.

This seems more reasonable in case of more rigid anatomical organs such as clavicles because their shapes do not vary too much and therefor there is no need to learn too many high abstract features. This architecture is called InvertedNet due to the way the numbers of feature maps are changed with respect to the original U-Net architecture.

d) All-Convolutional Network: Learning Pooling for Segmentation

J. T. Springenberg, A. Dosovitskiy, T. Brox, and M. Riedmiller, "Striving for simplicity: The all convolutional net," arXiv preprint arXiv:1412.6806, 2014 showed that having pooling layers replaced by convolutional layers with higher stride or removing pooling layers completely yields on similar or even improves results therefore making the network all-convolutional.

This modification introduces new parameters in the network but can be considered as a learning of pooling for each part of the network rather than just fixing pooling parameters to constant values.

Such pooling learning can be useful to make the network learn better features for smaller and thinner elongated objects. Further motivated by the work by J. T. Springenberg, A. Dosovitskiy, T. Brox, and M. Riedmiller, "Striving for simplicity: The all convolutional net," arXiv preprint arXiv:1412.6806, 2014, we consider their second configuration. In that configuration, each pooling layer is replaced by a convolutional layer with filter size equal to the pooling size of the replaced pooling layer. The All-Dropout architecture is modified correspondingly. This architecture is further called All-convolutional.

Training Strategies:

As already mentioned, large differences in sizes of anatomical organs of interest can introduce a problem of imbalanced data representation.

In such cases classes are represented in highly different amounts pixel-wise and therefore losses for sparsely represented classes can go unnoticed sometimes.

Hence classical formulations of loss such as cross-entropy or negative dice functions would underestimate the classes represented in very small amounts.

The problem related to the imbalance in pixel representation is solved in the present invention by introducing a weighted distance function.

Let C be the set of all ground-truth classes and N a partition of the used training set. For K∈N and $c_K$ its total pixel count we define $r_{K,1}$ as the ratio:

$$r_{K,1} := \frac{c_{l,K}}{c_K} \quad (1)$$

where $c_{l,K}$ is the number of pixels belonging to an organ class l∈C in the training batch K.

For a distance function d:$\{0,1\}^{m_1 \times m_2} \times \{0,1\}^{m_1 \times m_2} \to R$, and an image I∈K we minimize our target function $$\Lambda(L_{i,l})(I) := \sum_{l \in L} r_{K,l}^{-1} d(F(I)_l, L_{l,l}) \quad (2)$$

over the set K and the complete partition.

As a consequence, sparsely represented classes, e.g. clavicles, are no longer under-represented in favor to large ground-truth mask, e.g. lung fields.

For d we chose and evaluated the so-called weighted pixelwise cross-entropy and weighted negative dice loss functions.

The weighted dice loss function in our case takes the sigmoid activation computed at the final output feature map for each channel as the input. The sigmoid activation is defined as:

$$p_K(x) = \frac{1}{1 + e^{-a_K(x)}} \quad (3)$$

where $a_k(x)$ indicates activation at feature channel k at the pixel x∈I and $p_k(x)$ is the approximated probability of the pixel x not belonging to background. In the case of weighted negative dice the output does not have to provide a channel for the background class.

Given an image I, let $\{L_i\}$ be the set of non-background pixels in the corresponding ground-truth multi-channel mask and $$P_k(I) = \{x : x \in I \wedge p_k(x) - 1 | < \varepsilon\} \quad (4)$$

be the set of pixels where the model is sure that they do not belong to background and e is a small tolerance value.

The distance function d for the negative Dice coefficient for a training image I can then be defined as:

$$d_{L_{i,l}}(I) = -2 \frac{|P(I) \cap G(I)|}{|P(I)| + |G(I)|} \quad (5)$$

where P(I) is the predicted segmentation mask and G(I) is the corresponding ground-truth segmentation mask for the image I.

The weighted pixelwise cross-entropy takes the softmax activation computed at the final output feature map for each channel as the input. The softmax $p_k(x)$ can be defined as in the Ronneberger et al. "U-net: Convolutional networks for biomedical image segmentation," in International Conference on Medical Image Computing and Computer-Assisted Intervention, Springer, 2015, pp. 234-241; and the distance function d of the cross-entropy for a training image I is defined as:

$$d_{L_{i,l}}(I) = \sum_{x \in I} \frac{1_G(I) \log p_k(x)}{c_K} \quad (6)$$

Performance for both loss functions will be compared.

Proposed Network Architectures

Figure 1A:
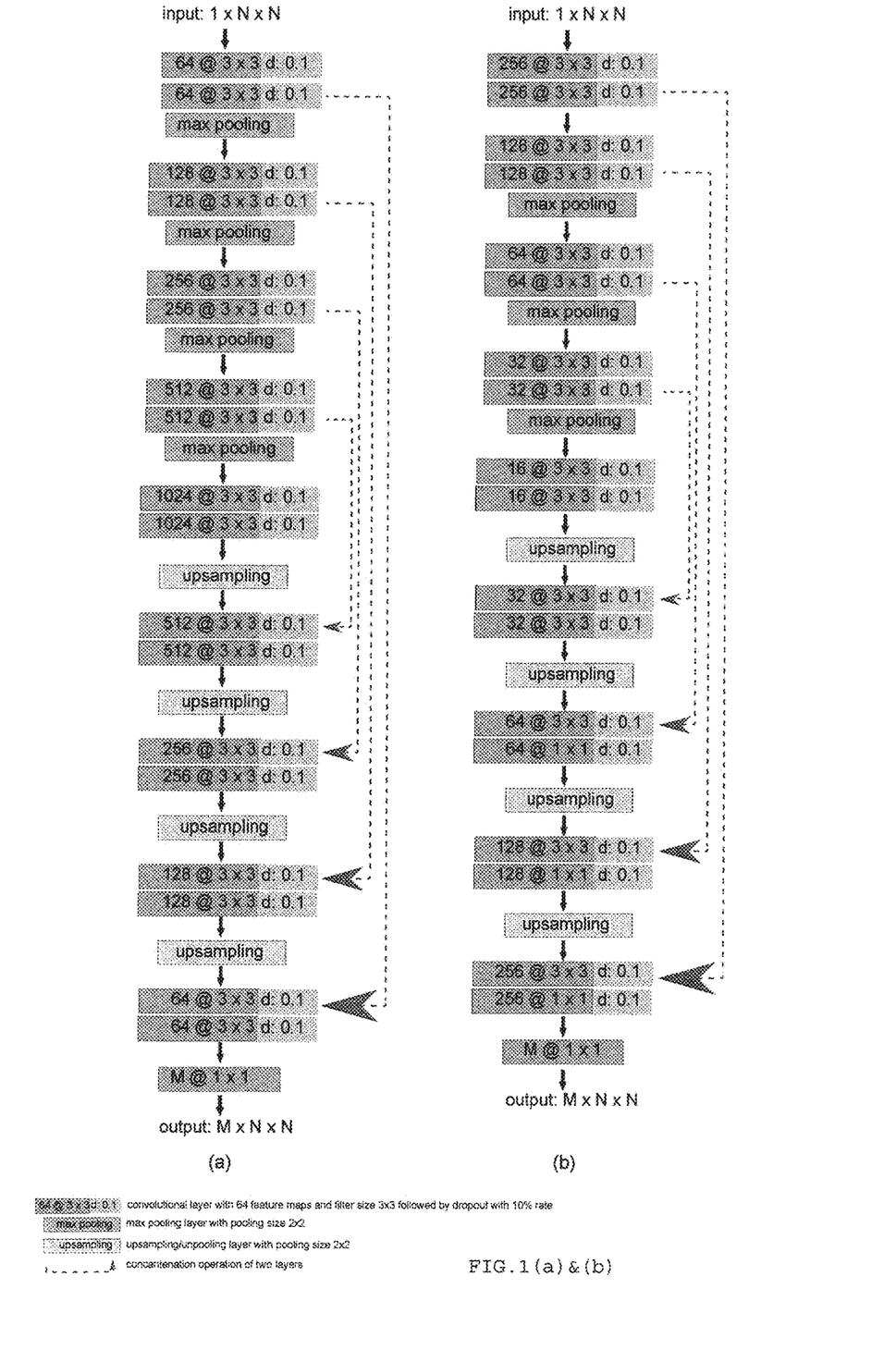
Figure 1C:
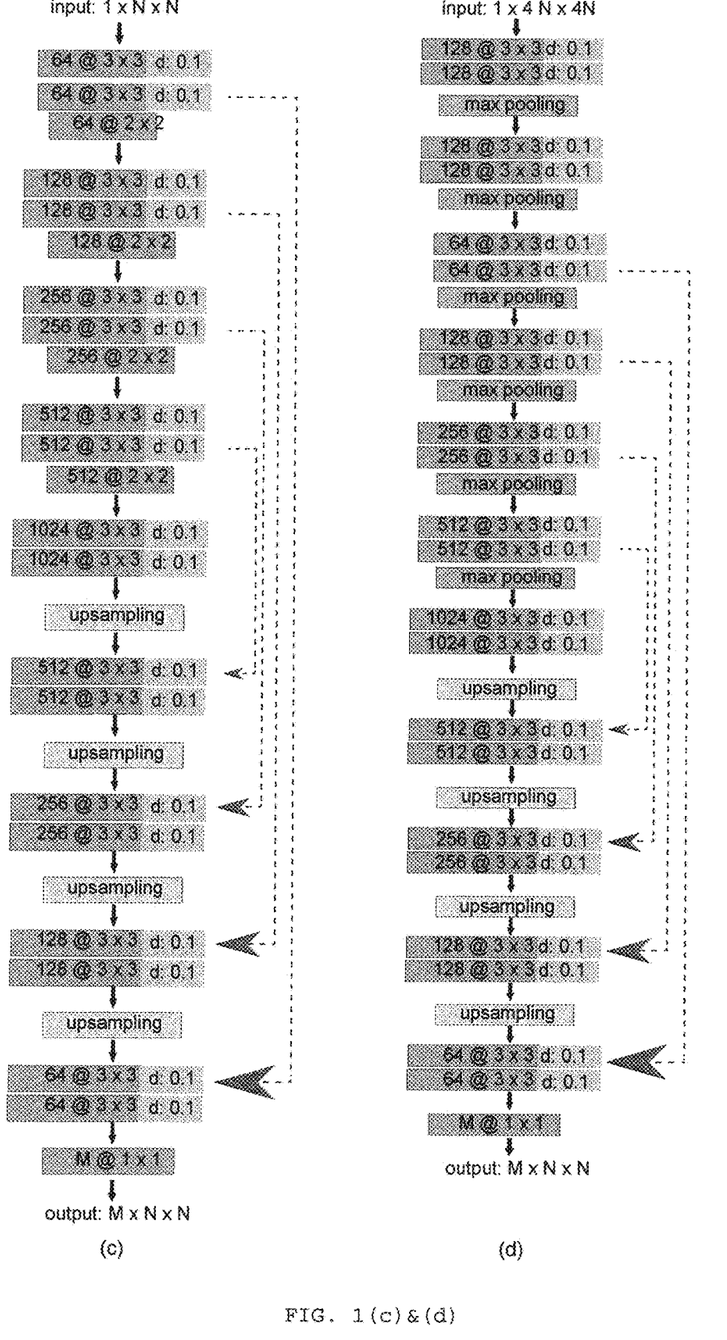
Figure 2:
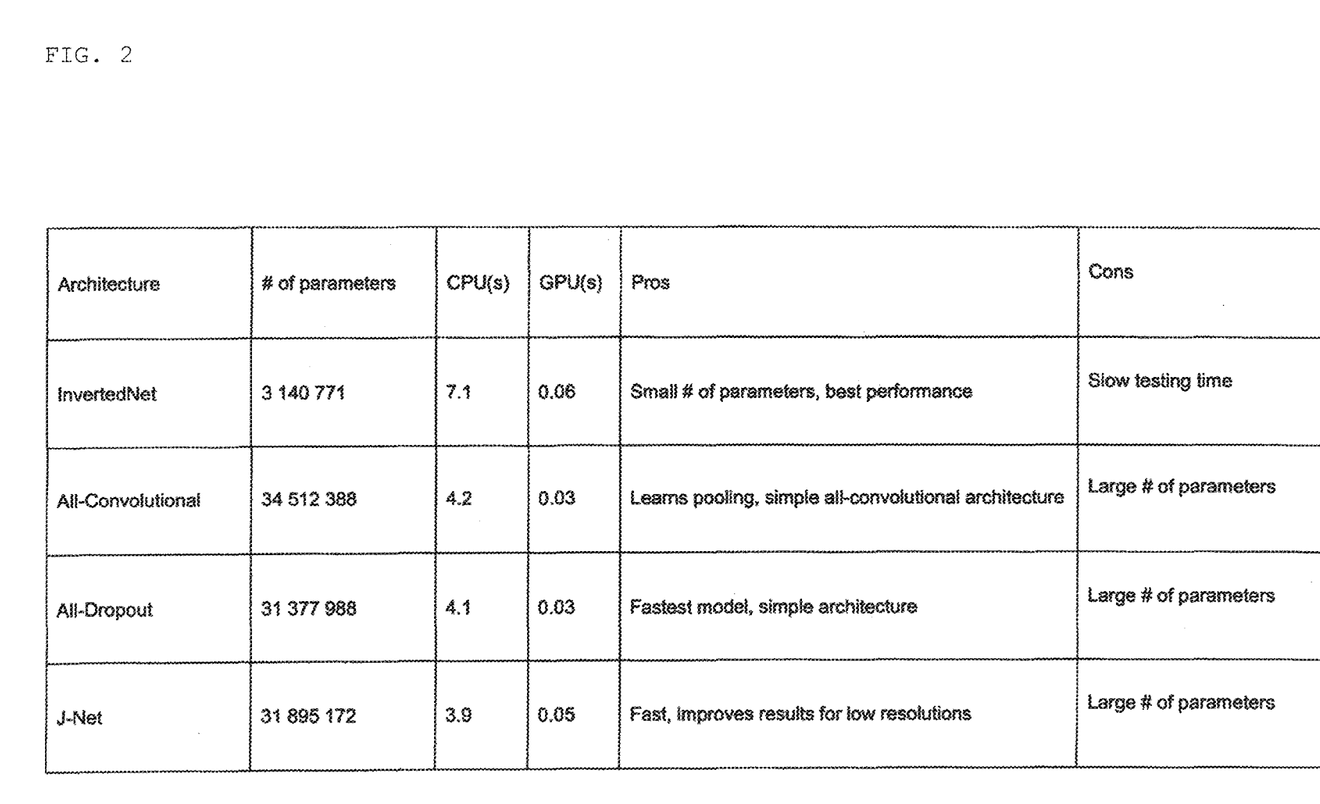
FIG. 2 shows the execution times for different image resolutions.

Different embodiments of the network architecture are shown in FIG. 1.

The proposed models in detail are as follows:

All-Dropout: Modified version of the U-Net architecture [Ronneberger et al. "U-net: Convolutional networks for biomedical image segmentation," in International Conference on Medical Image Computing and Computer-Assisted Intervention, Springer, 2015, pp. 234-241] with dropout layers placed after every convolutional layer. Shown at FIG. 1a.

InvertedNet: Similar to All-Dropout with the delayed subsampling of the first pooling layer and the numbers of feature maps in the network inverted with respect to original U-net. See FIG. 1b All-Convolutional: Similar to All-Dropout with pooling layers replaced by new convolutional layers with filter sizes equal to the pooling size of the corresponding pooling layer. See FIG. 1c J-Net: Similar to All-Dropout with the preceding four convolutional and two pooling layers and the input of a larger resolution. Shown at FIG. 1d Padded convolutions are used in all architectures for all convolutional layers. Therefore, output channels will have the same size as the input image except the J-net architecture where input dimensions are four times larger than of the output. All proposed architectures contain convolutional and dropout layers. In all architectures, all convolutional layers are followed by dropout layers except the third convolutional layers in the All-Convolutional architecture where the layer plays a role of a pooling layer it replaces.

In all models we used the rectified linear unit functions [R. H. Hahnloser et al., "Digital selection and analogue amplification coexist in a cortex-inspired silicon circuit," Nature, vol. 405, no. 6789, pp. 947-951, 200 [33]] at all convolutional hidden layers.

To reduce the number of parameters and speed up training, instead of the last dense layers a convolutional layer is used with the number of feature maps equal to the number of considered classes in case of the weighted dice function and with one or more background in case of weighted pixel-wise cross-entropy functions. To splash the values to the [0, 1] range at the output of the network, a sigmoid function is used as an activation at the output layer.

Experiments

JSRT Dataset

The JSRT dataset, J. Shiraishi, S. Katsuragawa, J. Ikezoe, T. Matsumoto, T. Kobayashi, K.-i. Komatsu, M. Matsui, H. Fujita, Y. Kodera and K. Doi, "Development of a digital image database for chest radiographs with and without a lung nodule; receiver operating characteristic analysis of radiologists' detection of pulmonary nodules," American Journal of Roentgentechnology, vol. 174, no. 1, pp. 71-74, 2000, is used both for training and evaluation. The dataset consists of 247 PA chest radiographs with a resolution of 2048×2048, 0.175 mm pixel size and 12 bit depth.

The SCR database with reference organ boundaries for left and right lung fields, heart and left and right clavicles were introduced in 1024×1024 resolution by Ginneken et al., "Segmentation of anatomical structures in chest radiographs using supervised methods: a comparative study on a public database," Medical Image Analysis, vol. 10, pp. 19-40, 2006.

Training Model

Data has been normalized using the mean and standard deviation across the whole training dataset. It has been zero-centered first by subtracting the mean and then normalized additionally by scaling using its standard deviation. It was then split into training and testing sets. All models were trained on images of the following image resolutions: 128×128, 256×256 and 512×512. Original images and masks were down-sampled to these resolutions by the local averaging algorithm. To make the paper comparable with state-of-the-art methods, most results in our work correspond to the 256×256 image resolution.

In all experiments the rectified linear unit functions R. H. Hahnloser et al., "Digital selection and analogue amplification coexist in a cortex-inspired silicon circuit," Nature, vol. 405, no. 6789, pp. 947-951, 200 were used at all convolutional hidden layers. It is the most common and well performing activation function in the modern network architectures.

To reduce number of parameters and speed up training in the end instead of using dense layer we used the convolutional layer with the number of feature maps equal to the number of considered classes in case of the weighted dice and with one more for background in case of weighted pixelwise cross-entropy functions. To splash the values to the {0,1} range at the output of the network we used sigmoid function as an activation at the output layer.

To optimize the model we used the Adaptive Moment Estimation method (ADAM) D. Kingma and J. Ba, "Adam: A method for stochastic optimization," arXiv preprint arXiv: 1412-6980, 2014 as it employs an adaptive learning rate approach for each parameter. It stores decaying average of both past squared gradients and past gradients. We have not performed an extensive evaluation of the methods but initial training runs showed that ADAM performed much better than other existing algorithms in terms of training convergence. We also varied different initial learning rates in order to find the most stable convergence and $10^{-5}$ $5*10^{-5}$ seemed to be the most reasonable choices. Training converged slower in the former but more stable than with the latter one. We therefore used the fixed initial rate of $10^{-5}$ in all our experiments.

Performance Metrics

To evaluate the architectures and compare with state-of-the-art works, we used the following performance metrics:

Dice Similarity Coefficient:

$$D_{si} = \frac{2 \times |G \cap S|}{|G| + |S|} \quad (9)$$

Jaccard Similarity Coefficient:

$$J = \frac{|G \cap S|}{|G| + |S| - |G \cap S|} \quad (10)$$

where in both coefficients $D_{si}$ and J, G represents the ground-truth data and S stands for the segmentation provided by the evaluated method.

Symmetric Mean Absolute Surface Distance:

$$S_{sg} = \frac{1}{(n_s + n_g)} \times \left( \sum_{i=1}^{n_s} |d_i^{sg}| + \sum_{j=1}^{n_g} |d_j^{gs}| \right) \quad (11)$$

where $n_s$ is the number of pixels in the segmentation provided by the evaluated method, $n_g$ is the number of pixels in the ground-truth data mask, $d_i^{sg}$ is the distance from i-th pixel in the segmentation to the closest pixel in the ground-truth data mask, and $d_j^{gs}$ is the distance from j-th pixel in the ground-truth data mask to the closest pixel in the segmentation provided by the evaluated method.

Results

Segmentation Performance

Figure 3:
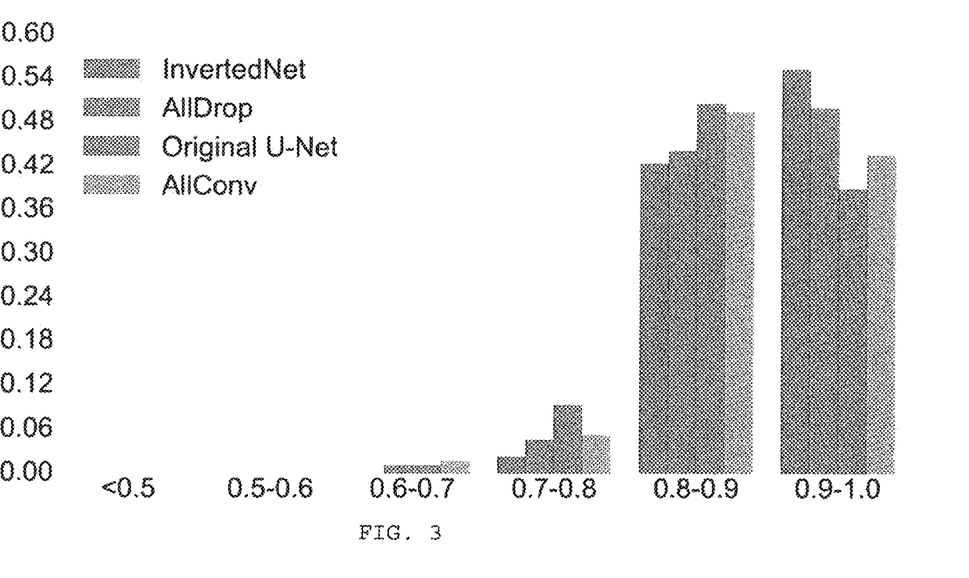
FIG. 3 is a comparison of the different embodiments of architectures used in a method according to the present invention versus state of the art methods.

Evaluation results for six proposed architectures for different resolutions are shown in FIG. 3. In addition, original U-Net architectures for three resolutions as well as the best performing methods and human observer introduced by Van Ginneken et al., "Segmentation of anatomical structures in chest radiographs using supervised methods, a comparative study on a public database," Medical Image Analysis, vol. 10, pp. 19-40, 2006, are added for comparison.

All results are subdivided into five blocks.

The first block contains only the human observer result.

The second block contains results for original U-Net architecture and methods proposed by Van Ginneken et al., "Segmentation of anatomical structures in chest radiographs using supervised methods, a comparative study on a public database," Medical Image Analysis, vol. 10, pp. 19-40, 2006.

The third, fourth and fifth block contain results of the original U-Net and the proposed architectures for three different resolutions.

Best results for each block are depicted in bold.

Scores for lung segmentation do not vary significantly. All methods were able to show a good performance. Though our architectures did not outperform human observed and the Hybrid Voting method, one of our models reached the same Jaccard score, and all of the proposed architectures as well as the original U-net achieved more accurate object contours according to the symmetric surface distance.

All proposed architectures reached the best symmetric distance to surface scores among all methods on all organs which proves that convolutional networks are very efficient in extracting features corresponding to object borders.

Even in case of quite low contras difference, for example on the borders between heart and lung or clavicles and lungs.

Clavicle segmentation is a bit more challenging task for all our architectures. And it is not surprising because clavicles are much smaller than heart and lungs and their shapes change more significantly from one scan to another. None of the proposed methods could outperform Human Observer. The automatic methods proposed by "Segmentation of anatomical structures in chest radiographs using supervised methods, a comparative study on a public database," Medical Image Analysis, vol. 10, pp. 19-40, 2006], have been outperformed though. The best proposed architecture outperformed Hybrid Voting by almost 8% in Jaccard overlap score. All our architectures performed better than the original U-Net architectures on all image resolutions.

In addition results for higher resolutions are much better for smaller objects such as clavicles. Except for InvertedNet architecture which showed a poor performance due to the delayed subsample pooling and small filter sizes in the convolutional layers. On lower resolutions though the InvertedNet demonstrated the best performance on the clavicle segmentation where Original U-Net was surpassed by more than 7% and the other two networks by 5% and 6% respectively. In summary, clavicles are more challenging for Original U-Net, All-Convolutional and All-Dropout on lower resolutions because of the multiple pooling layers in the contractive part of the network. Multiple pooling layers make such objects as clavicles become smaller and therefore smooth out borders between them. In this case the features extracted by the network become less expressive.

Heart segmentation was a challenging task for the InvertedNet architecture. It was even slightly outperformed by the Original U-Net which in its turn was surpassed by the other proposed architectures. Two other proposed architectures All-Convolutional and All-Dropout slightly surpassed the human observer on this task.

The performance of the overall best architecture InvertedNet has been evaluated with several splits of input data into training and testing sets.

Figure 4:
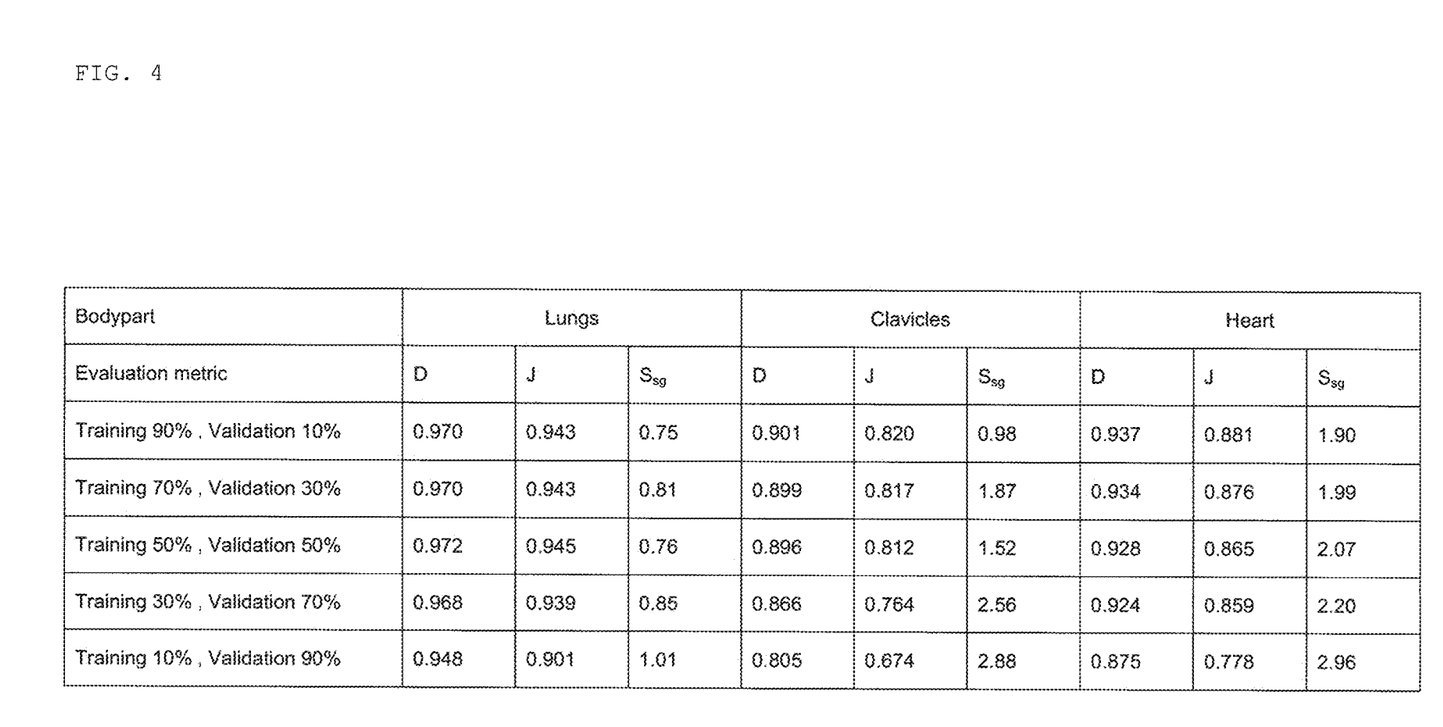
FIG. 4 is a comparison of the InvertNet architecture for different validation splits for Pixelwise Cross-Entropy Loss Function.
Figure 5:
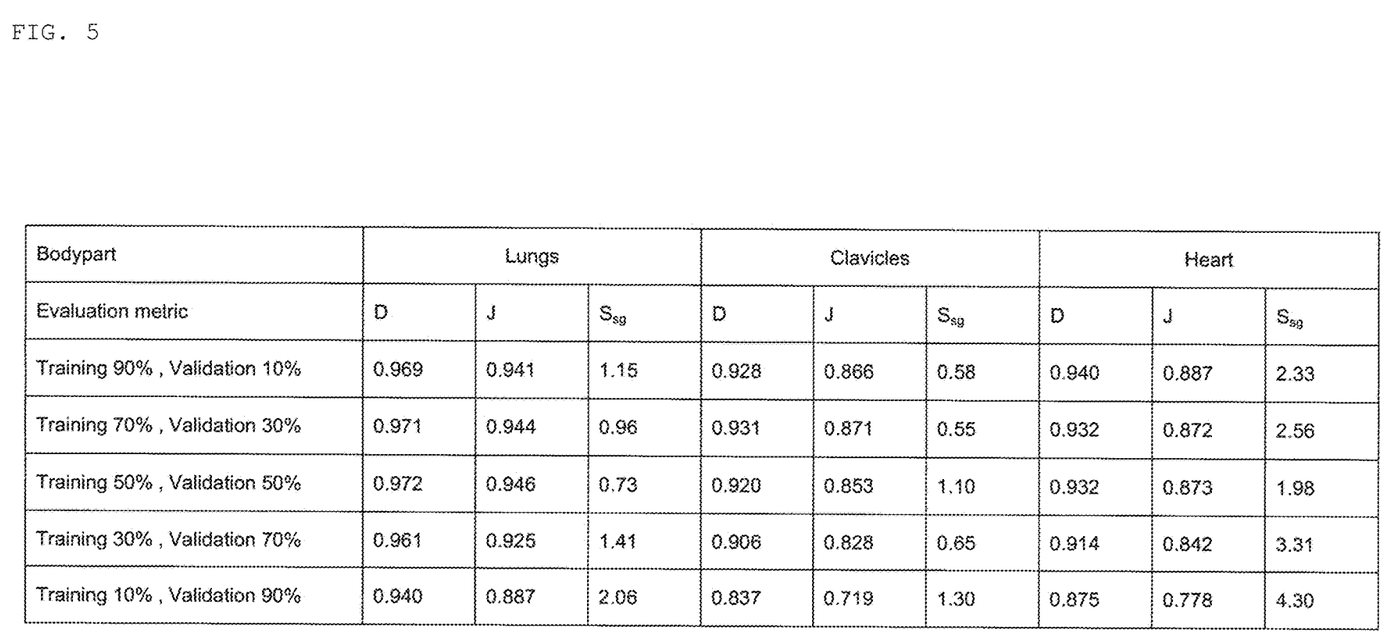
FIG. 5 is a comparison of the InvertNet architecture for different validation splits for Negative Dice Loss Function.

FIG. 4 shows testing results of the InvertedNet trained with the pixelwise cross-entropy loss function. As theoretically expected overall scores get improved when more training data is given to the network. On the other hand increasing difference between numbers of samples in training and testing sets leads to a slight overfitting on the data and therefore increasing of the final generalization error. This is not the case for the negative dice loss function though where clearly increasing number of training samples gives much better results. Evaluations results for different testing splits for the negative dice loss function are shown in FIG. 5.

With regard to the performance of the Original U-Net and the proposed models on the test set at each epoch during training, the scores of the Original U-Net typically grow faster than the other networks in the beginning but then reach a plateau and oscillate till the end of the training procedure. Other better regularized architectures though start off slower, reach higher or similar scores in the end. InvertedNet starts slow in the beginning but reaches the best result in the end.

Timing Performance

The method of the present invention is a very fast segmentation approach for chest radiographs. It can process thousands of images per day which could especially beneficial in big clinical environments when hundreds or sometimes thousands of people are being checked every day.

The invention claimed is:

1. A pipe-line method for multi-label segmentation of anatomical structures in a medical image, the method comprising:

training a convolutional neural network using a set of training data to obtain a set of optimal fixed weights; and segmenting anatomical structures in the medical image by using the convolutional neural network with the optimal fixed weights; wherein during the step of training, applying a weighted loss function to take into account under-representation of at least one of the anatomical structures included in a ground-truth mask relative to others of the anatomical structures; and an architecture of the convolutional neural network includes a U-net architecture modified to include a dropout layer provided after a convolution layer and pooling layers are replaced by convolution layers, and the convolution layers that have replaced the pooling layers have a filter size equal to a pooling size of the pooling layers that have been replaced.

2. The method according to claim 1, wherein the weighted loss function includes a weighted pixel-wise cross-entropy loss function, and the optimal fixed weights include parameters obtained as a result of optimizing the weighted loss function.

3. The method according to claim 1, wherein the weighted loss function includes a weighted negative dice loss function, and the optimal fixed weights include parameters obtained as a result of optimizing the weighted loss function.

4. The method according to claim 1, wherein the dropout layer includes a Gaussian dropout layer.

5. The method according to claim 1, wherein the architecture of the convolutional neural network consists only of convolutional, upsampling, and dropout layers.

6. A pipe-line method for multi-label segmentation of anatomical structures in a medical image, the method comprising:

training a convolutional neural network using a set of training data to obtain a set of optimal fixed weights; and segmenting anatomical structures in the medical image by using the convolutional neural network with the optimal fixed weights; wherein during the step of training, applying a weighted loss function to take into account under-representation of at least one of the anatomical structures included in a ground-truth mask relative to others of the anatomical structures; and an architecture of the convolutional neural network includes a U-net architecture modified to include a dropout layer after a convolution layer; subsampling of a first pooling layer is delayed; and feature maps in the convolutional neural network are inverted with respect to a U-net of the U-net architecture.

7. The method according to claim 6, wherein the weighted loss function includes a weighted pixel-wise cross-entropy loss function, and the optimal fixed weights include parameters obtained as a result of optimizing the weighted loss function.

8. The method according to claim 6, wherein the weighted loss function includes a weighted negative dice loss function, and the optimal fixed weights include parameters obtained as a result of optimizing the weighted loss function.

9. The method according to claim 6, wherein the dropout layer includes a Gaussian dropout layer.

* * * * *